United States Patent
Aubert

(10) Patent No.: US 11,559,086 B1
(45) Date of Patent: Jan. 24, 2023

(54) METHOD TO REMOTELY FIT BRASSIERES FOR PROSTHETICS WEARERS AND MASTECTOMY PATIENTS

(71) Applicant: Detra C. Aubert, Surprise, AZ (US)

(72) Inventor: Detra C. Aubert, Surprise, AZ (US)

( * ) Notice: Subject to any disclaimer, the term of this patent is extended or adjusted under 35 U.S.C. 154(b) by 203 days.

(21) Appl. No.: 15/469,209

(22) Filed: Mar. 24, 2017

Related U.S. Application Data

(60) Provisional application No. 62/312,715, filed on Mar. 24, 2016, provisional application No. 62/369,493, filed on Aug. 1, 2016.

(51) Int. Cl.
| | | |
|---|---|---|
| *A41C 3/00* | (2006.01) | |
| *A41H 1/02* | (2006.01) | |
| *A61F 2/12* | (2006.01) | |
| *G06Q 30/06* | (2012.01) | |
| *H04N 5/232* | (2006.01) | |
| *G06F 3/04842* | (2022.01) | |

(52) U.S. Cl.
CPC ............ *A41C 3/005* (2013.01); *A41H 1/02* (2013.01); *A61F 2/12* (2013.01); *G06Q 30/0631* (2013.01); *H04N 5/23206* (2013.01); *H04N 5/23216* (2013.01); *G06F 3/04842* (2013.01)

(58) Field of Classification Search
CPC .. A41C 3/005; A41H 1/02; A61F 2/12; G06Q 30/0631; H04N 5/23206; H04N 5/23216; G06F 3/04842
See application file for complete search history.

(56) References Cited

U.S. PATENT DOCUMENTS

| | | |
|---|---|---|
| 5,965,809 A | 10/1999 | Pechter |
| 7,162,441 B2 | 1/2007 | Nabarro |
| 7,164,962 B2 | 1/2007 | Petterson |
| (Continued) | | |

FOREIGN PATENT DOCUMENTS

| | | |
|---|---|---|
| CN | 103948196 | 7/2014 |
| CN | 103393245 | 4/2015 |

OTHER PUBLICATIONS

Cordier, Frederic & Seo, Hyewon & Thalmann, Nadia. (2003). Made-to-measure technologies for an online clothing store. Computer Graphics and Applications, IEEE. 23. 38-48. 10.1109/MCG.2003.1159612. (Year: 2003).*

(Continued)

*Primary Examiner* — Allison G Wood
*Assistant Examiner* — Ashley D Preston
(74) *Attorney, Agent, or Firm* — Hogan Lovells US LLP

(57) ABSTRACT

Embodiments include methods and systems to remotely and electronically enhance measurement accuracy and speed of electronic brassiere fitting data. A method according to an embodiment can include receiving a set of current user brassiere data from a remote user computing device, receiving a set of physiological images from the remote user computing device, and receiving brassiere fitting data from one or more data sources. The method can further include filtering the brassiere fitting data responsive to the set of current user brassiere data, and generating a first brassiere size responsive to filtering the brassiere fitting data. The method can further include modifying the first brassiere size responsive to the set of physiological images, and generating a recommended brassiere size responsive to modifying the first brassiere size.

10 Claims, 13 Drawing Sheets

(56) References Cited

U.S. PATENT DOCUMENTS

| | | | |
|---|---|---|---|
| 2009/0137894 A1 | 5/2009 | Olson | |
| 2010/0198607 A1 | 8/2010 | Nethero | |
| 2011/0218876 A1* | 9/2011 | Sorrentino | G06Q 30/0631 |
| | | | 705/26.7 |
| 2014/0019087 A1 | 1/2014 | Bengtson et al. | |
| 2014/0129375 A1* | 5/2014 | Coulter | G06Q 30/02 |
| | | | 705/26.7 |
| 2015/0154453 A1* | 6/2015 | Wilf | G06K 9/00711 |
| | | | 382/103 |
| 2017/0340024 A1* | 11/2017 | McKeen | A41C 3/142 |

OTHER PUBLICATIONS

Hanger Clinic, Inc., "Insignia Laser Scanning System", http://hangerclinic.com/limb-loss/adult-upper-extremity/Pages/Fitting-Casting-Insignia.aspx.

Thirdlove, "ThirdLove • Lingerie & Virtual Sizing Technology. The best bra is one you never think about", https://itunes.apple.com/us/app/thirdlove-get-sized-shop-perfect/id692635364?mt=8.

Thirdlove, "A killer combo of industry experience, fresh ideas, and a passion for fit", https://www.thirdlove.com/pages/about-us.

Thirdlove, FAQs, https://www.thirdlove.com/pages/faq.

Thirdlove, Bra Size Chart, https://www.thirdlove.com/pages/sizing-help.

Clare O'Connor, "Want A Bra That Fits Perfectly? This Billionaire Backed App Helps With Just Your iPhone", Forbes, Feb. 10, 2014.

Reuter's, "ThirdLove's Unique Technology Delivers Perfectly Fitting Apparel to Mobile Users", Aug. 14, 2013.

Ingrid Lunden, "Backed By $5.6M From NEA, a16z and More, ThirdLove Launches iOS App That Uses Selfies To Find The Best Bra For You", Nov. 7, 2013.

Michelle Persad, "ThirdLove' App Has An Uncanny Ability To Guess Your Bra Size", The Huffington Post, May 27, 2015.

* cited by examiner http://www._____.com

MEASUREMENTS

Please note that all images taken are used solely for our software to process and obtain your accurate measurements. The images are never saved or stored.

We will only store your measurement results if you choose to create an account for future purchases and only for 30 days.

○ Yes, please create an account and save my measurement results for future purchases.

○ No, do not create an account and store my measurements

[ CONTINUE ] — 416

124

402

FIG. 6 http://www._____.com

MEASUREMENTS

Begin by removing ONLY your top and bra, then:
- Stand facing your computer or laptop with your arms semi-down and relaxed as illustrated
- Make sure only your breasts appear on screen within the region bounded by the dotted lines

NOTE: ALL RECORDED IMAGING IS GATHERED ONLY WITHIN THE PERFORATED OUTLINE

- Once you are standing correctly as directed, an audio and/or on-screen command will instruct you to stand motionless while the first image is gathered for measurement
- Next, a command will direct you to begin rotating/turning slowly in place
- Continue turning slowly in place until a command directs you to stop
- Repeat this process following commands as directed
- Once all required imaging is successfully taken, you will hear and/or see a command confirm that the imaging process is complete

CONTINUE

FIG. 7 http://www._____.com

AVAILABLE BRA TYPES
- Push-up – enhance cleavage, lifts, and pushes breasts closer together
- Plunge – provides that WOW factor, enhances cleavage, pushes breasts together, ideal for low-cut tops, sacrifices some support, special event
- Full Support – covers entire breast, commonly used everyday
- T-Shirt – bust has smoother appearance, no raised seams, less visible when worn underneath tight-fitting tops
- Multiway – straps are versatile; straps can be worn, e.g., one shoulder, low back, halter, both removed, and standard with both straps; ideal for day or evening garments
- Demi – provides fabulous cleavage due to half cup size, less breast coverage (cut is approximately one inch above nipple), less support, lifts breasts, more popular of bra types, ideal for low cut garments
- Mastectomy – for women who have one or no breast, prosthesis
- Nursing – cups made with front flaps that unclamp and fold downward, providing quick and easy access to nipples for infant
- Halter – straps clasp behind neck and back, provides approximately 80 percent breast coverage
- Padded – ideal for small breasts, enhances fullness, padding sewn into fabric, creates more cleavage
- U- Plunge – perfect for deep plunging garments, creates cleavage
- Silicon Gel-Filled – bra cups filled with silicon gel to give breasts a larger appearance, ideal for small breasts

FIG. 9

| BAND MINUS BUST DIFFERENCE | US CUP SIZES | EUROPEAN | UK |
|---|---|---|---|
| LESS THAN 1" | AA | AA | AA |
| 1" | A | A | A |
| 2" | B | B | B |
| 3" | C | C | C |
| 4" | D | D | D |
| 5" | DD/E | E | DD |
| 6" | DDD/F | F | E |
| 7" | DDDD/G | G | F |
| 8" | DDDDD/H | H | FF |
| 9" | DDDDDD/I | I | G |
| 10" | J | J | GG |
| 11" | K | | H |
| 12" | L | | HH |
| 13" | M | | J |
| 14" | N | | JJ |

FIG. 10

| BRA SIZE | AA | A | B | C | D | DD | DDD | G | GG | H |
|---|---|---|---|---|---|---|---|---|---|---|
| | | | | | | | 54 | 52 | 50 | 48 |
| | | | | | | 54 | 52 | 50 | 48 | 46 |
| | | | | | 54 | 52 | 50 | 48 | 46 | 44 |
| | | | | 54 | 52 | 50 | 48 | 46 | 44 | 42 |
| | | | | 52 | 50 | 48 | 46 | 44 | 42 | 40 |
| | | | 52 | 50 | 48 | 46 | 44 | 42 | 40 | 38 |
| | | | 50 | 48 | 46 | 44 | 42 | 40 | 38 | |
| | | | 48 | 46 | 44 | 42 | 40 | 38 | | |
| | | 48 | 46 | 44 | 42 | 40 | 38 | | | |
| | 48 | 46 | 44 | 42 | 40 | 38 | 36 | | | |
| | 46 | 44 | 42 | 40 | 38 | 36 | 34 | | | |
| | 44 | 42 | 40 | 38 | 36 | 34 | | | | |
| | 42 | 40 | 38 | 36 | 34 | 32 | | | | |
| | 40 | 38 | 36 | 34 | 32 | | | | | |
| | 38 | 36 | 34 | 32 | 30 | | | | | |
| | 36 | 34 | 32 | 30 | | | | | | |
| | 34 | 32 | 30 | | | | | | | |
| | 32 | 30 | | | | | | | | |
| | 30 | | | | | | | | | |

FIG. 11

| Cup Size | BRA SIZE | | | | | | | | |
|---|---|---|---|---|---|---|---|---|---|
| | 32 | 34 | 36 | 38 | 40 | 42 | 44 | 46 | 48 |
| A | 2 | 3 or 4 | 5 or 6 | 7 or 8 | | | | | |
| B | 3 or 4 | 5 or 6 | 7 or 8 | 8 or 9 | 9 or 10 | 9 or 10 | 10 or 11 | 10 or 11 | 11 or 12 |
| C | 4 or 5 | 6 or 7 | 8 or 9 | 9 or 10 | 9 or 10 | 10 or 11 | 11 | 11 or 12 | 11 or 12 |
| D | 5 or 6 | 7 or 8 | 9 or 10 | 10 or 11 | 11 | 11 | 11 or 12 | 11 or 12 | 12 or 14 |
| DD | 6 or 7 | 8 or 9 | 10 or 11 | 11 or 12 | 11 or 12 | 11 or 12 | 12 | 12 | 14 or 16 |

FIG. 12

METHOD TO REMOTELY FIT BRASSIERES FOR PROSTHETICS WEARERS AND MASTECTOMY PATIENTS

RELATED APPLICATIONS

This application claims priority to and the benefit of U.S. Provisional Patent Application No. 62/312,715, titled "Scanner Application," filed Mar. 24, 2016, and U.S. Provisional Patent Application No. 62/369,493, titled "Systems and Methods to Remotely Fit Brassieres for Prosthetics Wearers and Mastectomy Patients," filed Aug. 1, 2016, each of which is hereby incorporated by reference.

FIELD OF INVENTION

Embodiments relate to fitting garments for prosthetics wearers and mastectomy patients.

BACKGROUND

Most women wear brassieres that do not fit properly and are either too large or too small. This problem of poor fit is magnified for mastectomy patients, prosthetics wearers, and other amputees, who often need modified sizes and brassiere shapes for a proper fit. Customized brassieres are not widely accessible, however, and require detailed individual measurements to design.

SUMMARY

Embodiments of systems, computer-readable media, interfaces, and methods advantageously can provide an application that will assist with customization of bras for women, specifically for those women who wear prosthetics, like veterans and cancer survivors. Embodiments can be used to obtain an accurate cup size and back and shoulder measurements. Obtaining accurate measurements can allow for the creation of a customized brassiere (bra).

Embodiments also can include a customer questionnaire that queries, for example, present weight and garment type that will be worn with the bra, in order to define a desired effect for the bra. After successfully obtaining customer measurements and a completed questionnaire, a window can be displayed to the customer that includes any and all bra style(s) that will best achieve the user's desired effect and look. Embodiments thus can be suitable for a variety of women, including petite women, average-sized women, nursing mothers, full-figured women, and women who have had a mastectomy or have a deformity.

For example, an embodiment can include a remote electronic method to enhance measurement accuracy and speed of electronic brassiere fitting data. Such a method can include receiving a set of current user brassiere data from a remote user computing device and receiving a set of physiological images from the remote user computing device. A method further can include receiving brassiere fitting data from one or more data sources, filtering the brassiere fitting data responsive to the set of current user brassiere data, and generating a first brassiere size responsive to filtering the brassiere fitting data. A method still further can include modifying the first brassiere size responsive to the set of physiological images and generating a recommended brassiere size responsive to modifying the first brassiere size.

Another method can include displaying a user interface to a remote user computing device. The remote user computing device can be associated with a user who wears a prosthetic device or has had a mastectomy. Further, the remote user computing device can be in communication with one or more imaging devices. The user interface also can be formatted to display information associated with brassiere fit and to receive input from the remote user computing device.

A method also can include receiving a set of current user brassiere data from the remote user computing device via the Internet. The set of data can include one or more of: the user's name, the user's email address, the user's home address, the user's age, outfit parameters, the user's current brassiere size, mastectomy information, and prosthetic information, for example.

A method further can include transmitting imaging instructions to the remote user computing device via the Internet. The imaging instructions, for instance, can include one or more audio commands and commands displayed on the user interface. Additionally, a method can include receiving, using the one or more imaging devices and via the Internet, a set of physiological images of the user from the remote user computing device.

A method also can include receiving brassiere fitting data from one or more data sources and filtering the brassiere fitting data responsive to the set of data. Further, a method can include generating a first brassiere size responsive to filtering the brassiere fitting data and modifying the first brassiere size responsive to the set of physiological images. A method then can include generating a recommended brassiere size responsive to modifying the first brassiere size and transmitting the recommended brassiere size to the remote user computing device via the Internet. A method additionally can include updating the user interface to display the recommended brassiere size and one or more brassiere recommendations on the remote user computing device.

In some instances, the one or more imaging devices can include one or more of: a camera, a three-dimensional body scanner, an X-ray imaging device, a millimeter wave imaging device, and a magnetic resonance imaging device. Further, the set of physiological images can include 360 degree images of the user's torso. Additionally, the brassiere fitting data can include, for each available brassiere size, a set of ranges of: torso circumference measurements, bust circumference measurements, and shoulder to bust measurements.

In some circumstances, generating the recommended brassiere size can include comparing the brassiere fitting data and the set of physiological images to the set of ranges for each available brassiere size. In addition, the outfit parameters can include one or more garment types, one or more garment styles, and one or more garment colors. The one or more brassiere recommendations also can include purchasing information for one or more brassieres.

Another remote electronic method to enhance measurement accuracy and speed of electronic brassiere fitting data according to an embodiment can include displaying a user interface to a remote user computing device associated with a user who wears a prosthetic device or has had a mastectomy. The remote user computing device can be in communication with one or more imaging devices, and the user interface can be formatted to receive input from the remote user computing device. A method can include receiving, using the one or more imaging devices, a set of physiological images of the user from the remote user computing device. Further, a method can include generating a recommended brassiere size responsive to receipt of brassiere fitting data from one or more data sources and the set of physiological images. A method then can include updating the user interface to display the recommended brassiere size and one or more brassiere recommendations on the remote user computing device.

Additionally, in some instances, the one or more imaging devices can include one or more of: a camera, a three-dimensional body scanner, an X-ray imaging device, a millimeter wave imaging device, and a magnetic resonance imaging device. Further, the set of physiological images can include 360 degree images of the user's torso. The brassiere fitting data can include, for each available brassiere size, a set of ranges of: torso circumference measurements, bust circumference measurements, and shoulder to bust measurements. Additionally, generating the recommended brassiere size can include comparing the brassiere fitting data and the set of physiological images to the set of ranges for each available brassiere size. In some instances, the method further can include receiving a set of current user brassiere data from the remote user computing device. The set of data can include one or more of: the user's name, the user's email address, the user's home address, the user's age, outfit parameters, the user's current brassiere size, mastectomy information, and prosthetic information. Additionally, the outfit parameters can include one or more garment types, one or more garment styles, and one or more garment colors, and the one or more brassiere recommendations can include purchasing information for one or more brassieres.

Embodiments also can include systems. A system to remotely and electronically enhance measurement accuracy and speed of electronic brassiere fitting data according to an embodiment, for example, can include one or more processors and a non-transitory computer-readable medium in communication with the one or more processors. The non-transitory computer-readable medium can have one or more computer programs stored therein that, when executed by the one or more processors, cause the system to take certain actions. For example, the system can display a user interface to a remote user computing device associated with a user who wears a prosthetic device or has had a mastectomy. The remote user computing device can be in communication with one or more imaging devices, and the user interface can be formatted to receive input from the remote user computing device. The system also can receive, using the one or more imaging devices, a set of physiological images of the user from the remote user computing device and generate a recommended brassiere size responsive to receipt of brassiere fitting data from one or more data sources and the set of physiological images. Further, the system can update the user interface to display the recommended brassiere size and one or more brassiere recommendations on the remote user computing device.

In another example, a system can receive a set of physiological images from a remote user computing device, receive brassiere fitting data from one or more data sources, and generate a recommended brassiere size responsive to receipt of the brassiere fitting data and the set of physiological images.

In some circumstances, the one or more imaging devices can include one or more of: a camera, a three-dimensional body scanner, an X-ray imaging device, a millimeter wave imaging device, and a magnetic resonance imaging device, and the set of physiological images can include 360 degree images of the user's torso. Additionally, the brassiere fitting data can include, for each available brassiere size, a set of ranges of: torso circumference measurements, bust circumference measurements, and shoulder to bust measurements. The recommended brassiere size can include comparing the brassiere fitting data and the set of physiological images to the set of ranges for each available brassiere size.

In some instances, the one or more computer programs, when executed by the one or more processors, further can cause the system to receive a set of current user brassiere data from the remote user computing device. The set of data can include one or more of: the user's name, the user's email address, the user's home address, the user's age, outfit parameters, the user's current brassiere size, mastectomy information, and prosthetic information. Further, the outfit parameters can include one or more garment types, one or more garment styles, and one or more garment colors, and the one or more brassiere recommendations can include purchasing information for one or more brassieres.

BRIEF DESCRIPTION OF DRAWINGS

These and other features, aspects, and advantages of the present invention will become better understood with regard to the following descriptions, claims, and accompanying drawings. It is to be noted, however, that the drawings illustrate only several embodiments of the invention and are therefore not to be considered limiting of the invention's scope as it can admit to other equally effective embodiments.

FIG. 6 is a schematic diagram of an interface according to an embodiment of the invention.

FIG. 7 is a schematic diagram of an interface according to an embodiment of the invention.

FIG. 9 is a schematic diagram of an interface according to an embodiment of the invention.

FIG. 10 is a chart according to an embodiment of the invention.

FIG. 11 is a chart according to an embodiment of the invention.

FIG. 12 is a chart according to an embodiment of the invention.

DETAILED DESCRIPTION

So that the manner in which the features and advantages of the embodiments of systems, computer-readable media, interfaces, and methods of the present invention, as well as others, which will become apparent, may be understood in more detail, a more particular description of the embodiments of systems, computer-readable media, interfaces, and methods of the present invention briefly summarized above may be had by reference to the embodiments thereof, which are illustrated in the appended drawings, which form a part of this specification. It is to be noted, however, that the drawings illustrate only various embodiments of the embodiments of systems, computer-readable media, interfaces, and methods of the present invention and are therefore not to be considered limiting of the embodiments of systems, computer-readable media, interfaces, and methods of the present invention's scope as it may include other effective embodiments as well.

Embodiments can include methods, systems, computer-readable media, and interfaces. For example, an embodiment can include a method to remotely fit brassieres, such as a remote electronic method to enhance measurement accuracy and speed of electronic brassiere fitting data. Embodiments advantageously can provide practical uses in the accuracy of measurement for prosthetics, including breast(s) due to mastectomy or body deformity and human limbs due to amputation or body deformity, such as legs, arms, and feet, for example.

Figure 1:
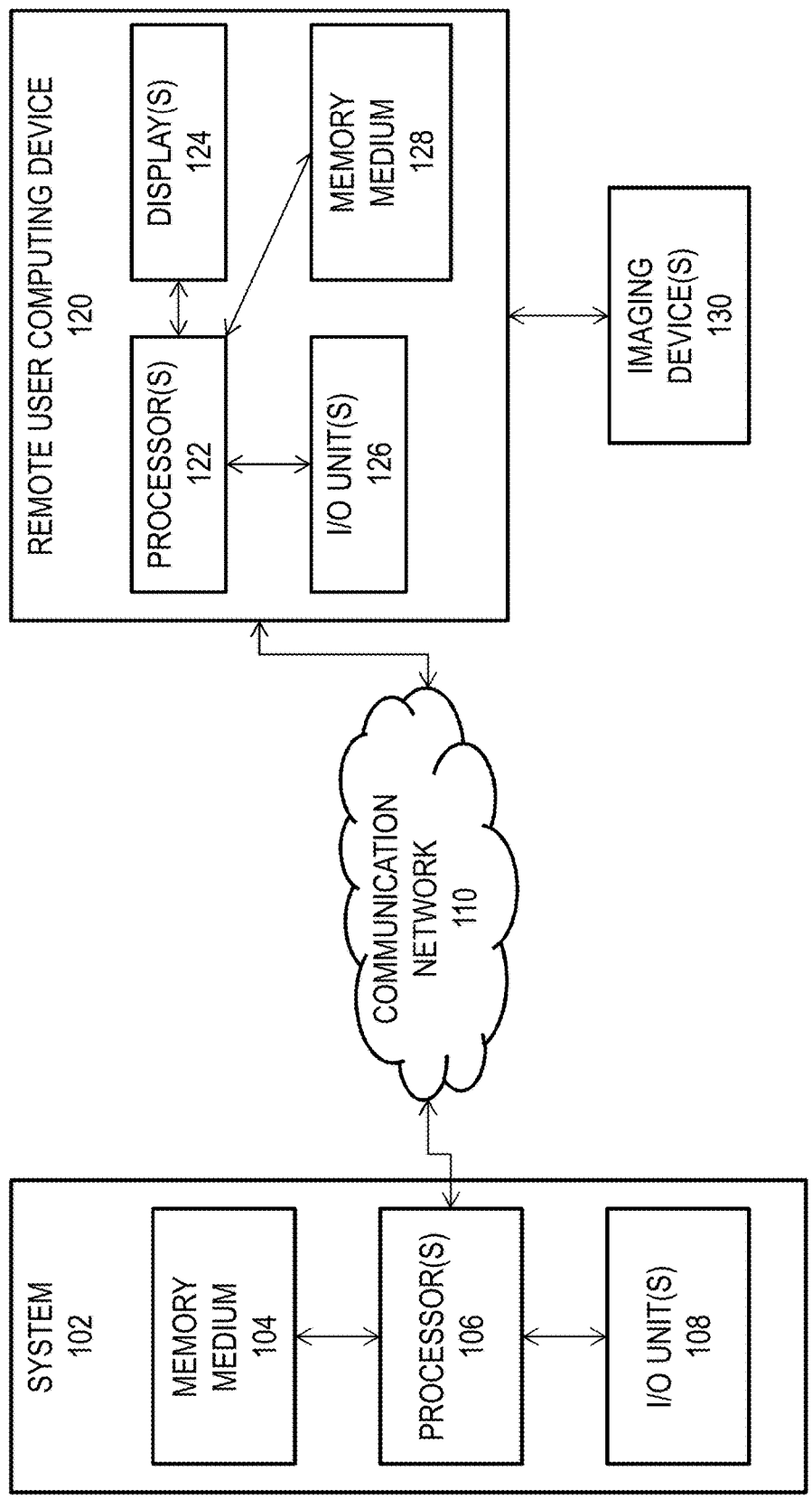
FIG. 1 is a schematic diagram of a system according to an embodiment of the invention.

Such a method can include displaying a user interface at a remote user computing device 120, as illustrated in FIG. 1, for example, associated with a user who wears a prosthetic device or has had a mastectomy. An exemplary remote user computing device 120 can be, for example, a laptop or desktop computer, a tablet, or a smartphone. An exemplary user interface 402 as displayed on a display 124 is illustrated in FIGS. 4-8, for instance.

Figure 4:
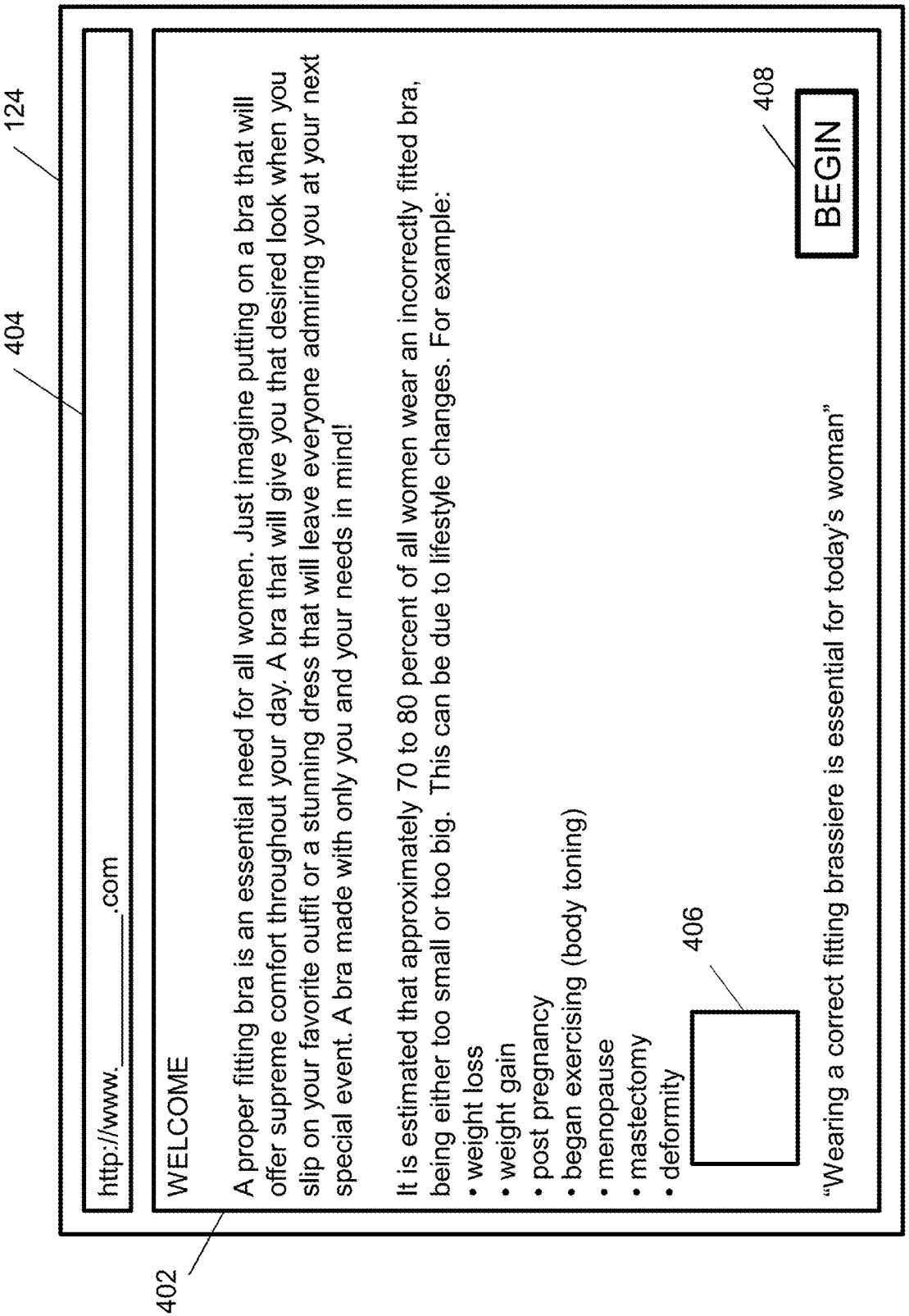
FIG. 4 is a schematic diagram of an interface according to an embodiment of the invention.
Figure 5A:
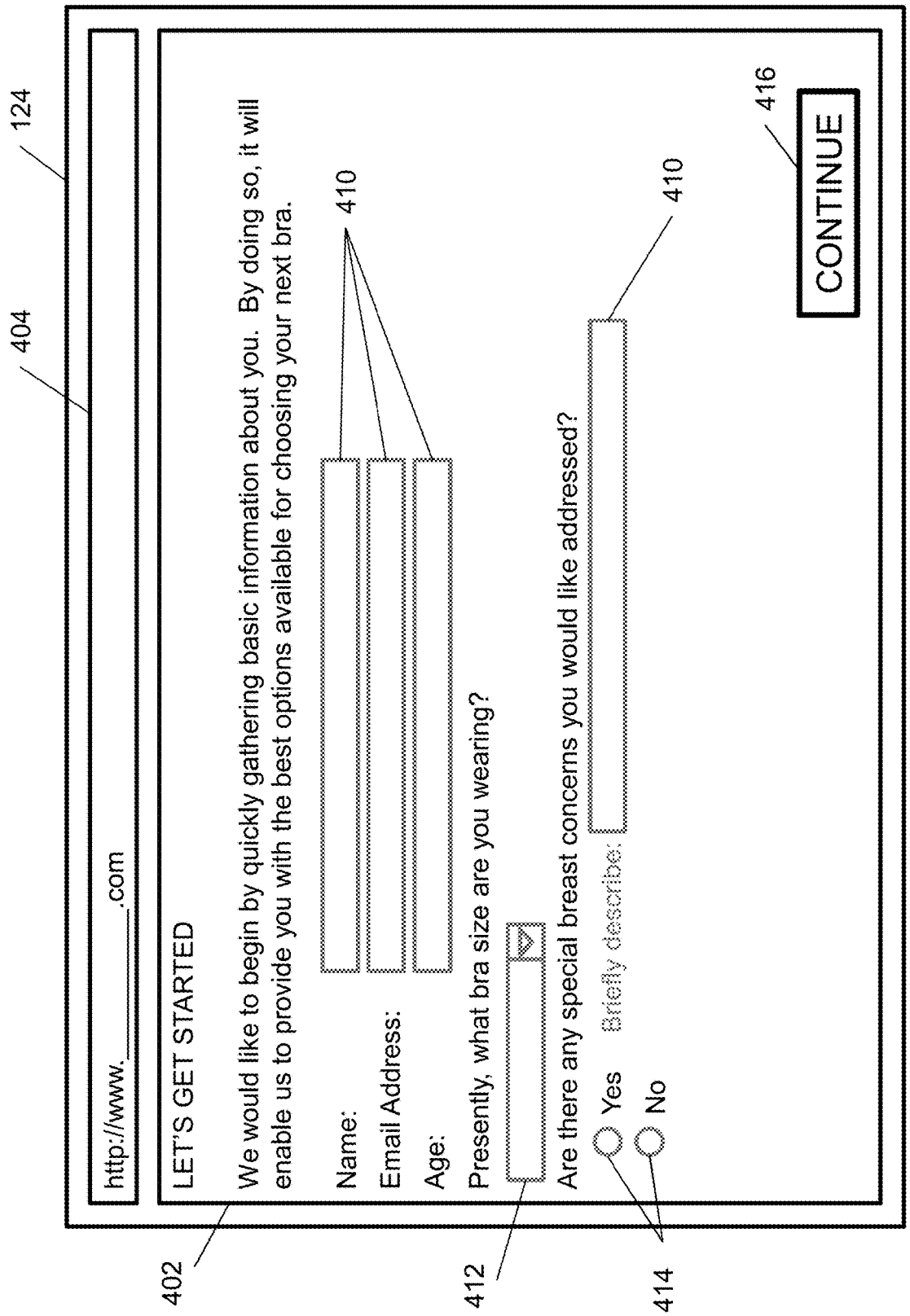
FIG. 5A-B is a schematic diagram of an interface according to an embodiment of the invention.

The remote user computing device 120 can be in communication with one or more imaging devices 130. For example, the one or more imaging devices 130 can include a camera, a three-dimensional body scanner, an X-ray imaging device, a millimeter wave imaging device, a magnetic resonance imaging device, other imaging devices, and combinations of any of the foregoing. The one or more imaging devices 130 further can be built into the remote user computing device 120, or the one or more imaging devices 130 can be peripheral components connected to the remote user computing device 120. The user interface 402 can be formatted to display information associated with brassiere fit and to receive input from the remote user computing device 120, as illustrated in FIGS. 4-5, for example.

A method further can include receiving a set of current user brassiere data from the remote user computing device 120 via the Internet or other communication network 110. The set of current user brassiere data can include, for example: the user's name, the user's email address, the user's home address, the user's age, outfit parameters, the user's current brassiere size, mastectomy information, prosthetic information, and any combination of the foregoing. In some circumstances, the outfit parameters can include one or more garment types, one or more garment styles, one or more garment colors, and one or more garment fabric parameters. For example, outfit parameters can include garment styles such as neckline (halter strap, halter, high neckline, straight, spaghetti strap, scoop, Queen Anne, cowl, sweetheart, bateau, v-neck, Sabrina, asymmetric, square, illusion, jewel, for example) and garment fabric parameters such as smooth or textured. An example of a user interface 402 configured to receive a set of data is illustrated in FIG. 5, for instance.

Additionally, a method according to an embodiment can include transmitting imaging instructions to the remote user computing device 120 via the Internet. The imaging instructions can include one or more audio commands and commands displayed on the user interface 402, for example, such as the instructions displayed on the user interface 402 in FIG. 7. A method then can include receiving a set of physiological images of the user from the remote user computing device 120 using the one or more imaging devices 130 and via the Internet. In some circumstances, the set of physiological images can include 360 degree images of the user's torso, for example.

A method also can include receiving brassiere fitting data from one or more data sources. For example, the brassiere fitting data can include, for each available brassiere size, a set of ranges of: torso circumference measurements, bust circumference measurements, and shoulder to bust measurements. The brassiere fitting data can be filtered responsive to the set of current user brassiere data. Further, a first brassiere size can be generated responsive to filtering the brassiere fitting data.

A method then can include modifying the first brassiere size responsive to the set of physiological images and generating a recommended brassiere size responsive to modifying the first brassiere size. For example, in some instances, generating the recommended brassiere size can include comparing the brassiere fitting data and the set of physiological images to the set of ranges for each available brassiere size.

Figure 8:
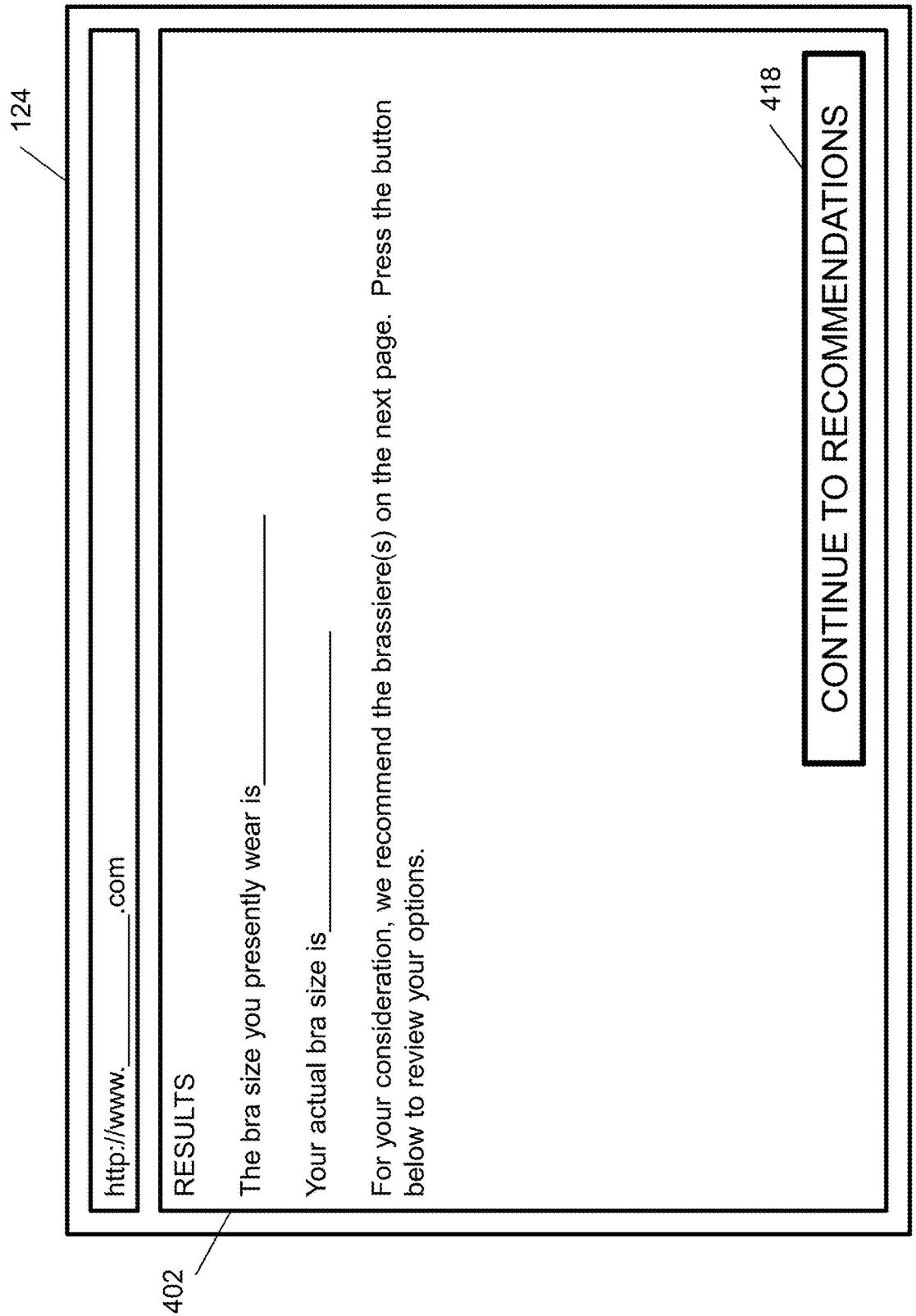
FIG. 8 is a schematic diagram of an interface according to an embodiment of the invention.

In addition, a method can include transmitting the recommended brassiere size to the remote user computing device 120 via the Internet and updating the user interface 402 to display the recommended brassiere size and one or more brassiere recommendations on the remote user computing device 120, as illustrated in FIG. 8, for example. In some instances, the one or more brassiere recommendations can include purchasing information for one or more brassieres, for example.

Figure 2:
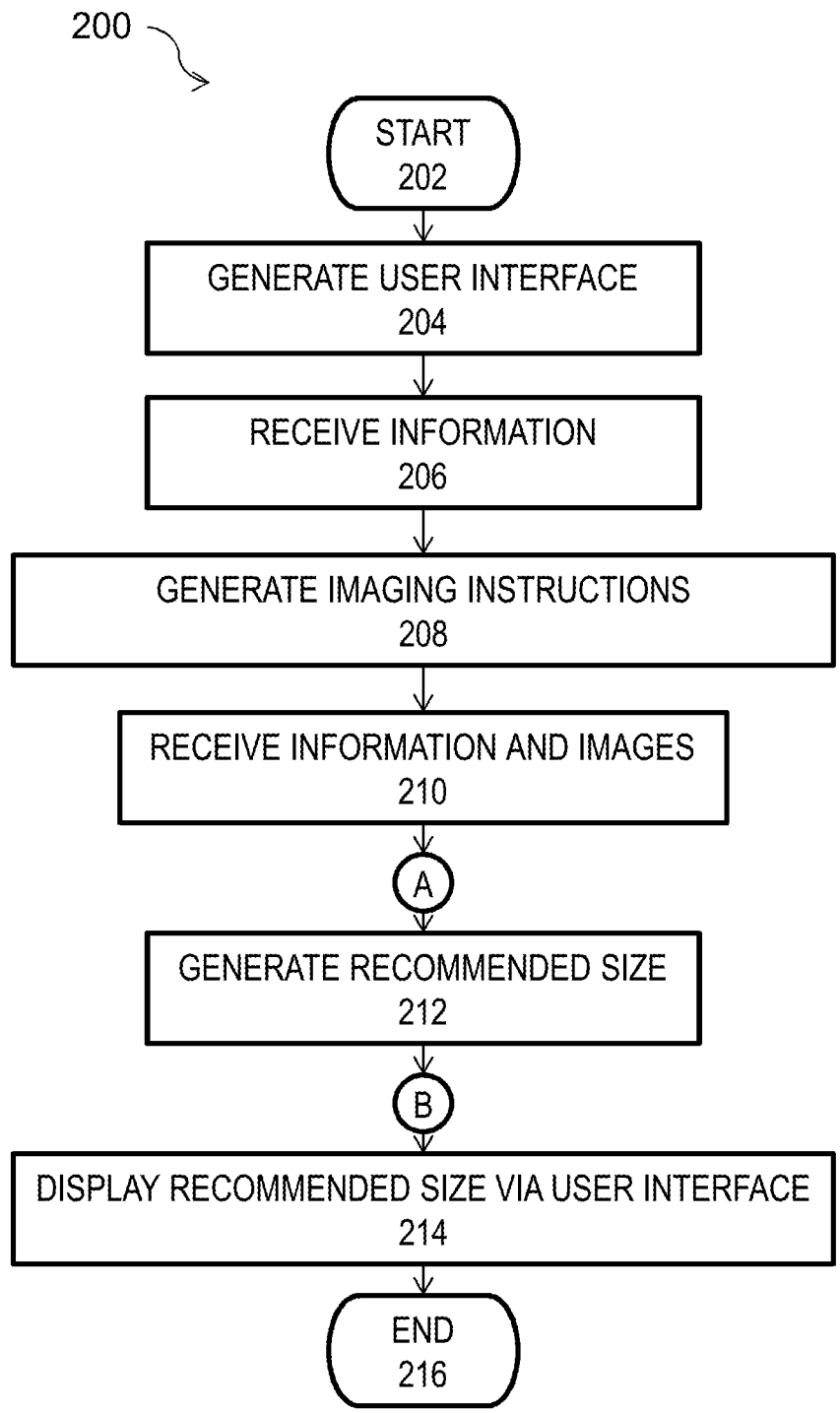
FIG. 2 is a schematic diagram of a method according to an embodiment of the invention.
Figure 3:
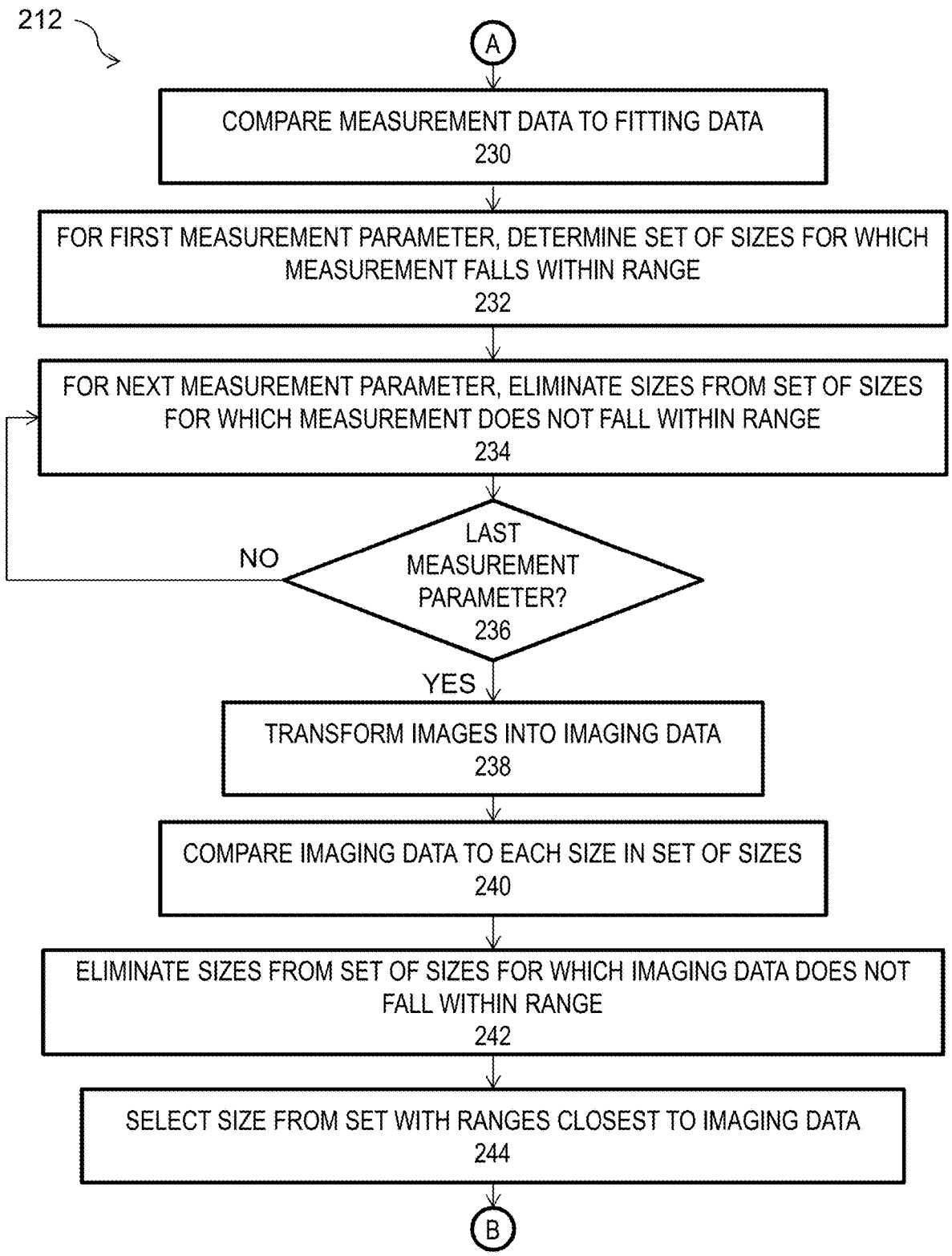
FIG. 3 is a schematic diagram of a method according to an embodiment of the invention.

An exemplary method 200 according to an embodiment is illustrated in FIGS. 2-3, for example. After starting at step 202 of FIG. 2, a method 200 can include generating a user interface at step 204 on a remote user computing device 120 and receiving information at step 206 from the remote computing device 120, including without limitation information about the user's having had a mastectomy and information about prosthetics worn by the user. A method 200 then can include generating imaging instructions at step 208, such as audio commands and commands displayed on user interface 402, as illustrated in FIG. 7, for example. A method 200 further can include receiving information and images at step 210 from the remote user computing device 120. Additionally, a method 200 can include generating a recommended brassiere size at step 212, which is further illustrated in FIG. 3, for example. A method 200 then can include displaying the recommended size via a user interface 402 at step 214 before ending at step 216.

As illustrated in FIG. 3, an example method to generate a recommended brassiere size 212 can include comparing measurement data provided by the user to fitting data (including without limitation brassiere sizing information associated with ranges of measurement information) at step 230, for example. A method 212 then can include analyzing each measurement parameter included in the measurement data (such as the user's reported torso circumference measurements, bust circumference measurements, and shoulder to bust measurements) to determine brassiere sizes for which the measurement falls into the size's respective range(s).

For example, at step 232, a set of sizes can be determined for which the user's measurement of a first measurement parameter (such as torso circumference measurements, bust circumference measurements, and shoulder to bust measurements) falls within the respective sizes' ranges. At step 234, for the next measurement parameter (such as torso circumference measurements, bust circumference measurements, and shoulder to bust measurements), any size(s) in the set of sizes for which the user's measurement does not fall within the range of the respective size(s) can be eliminated from the set of sizes.

Then, at step 236, a method 212 can include determining whether the measurement parameter analyzed in step 234 is the last measurement parameter. If it is not the last measurement parameter at step 236, a method 212 can include analyzing the next measurement parameter at step 234 to eliminate any additional size(s) from the set of sizes. If the measurement parameter analyzed in step 234 is determined to be the last measurement parameter at step 236, a method 212 can include transforming images of the user into imaging data at step 238. Such imaging data can include, for example, simulated measurements of the user's body dimensions in order to be used to calculate the strap and cup size accurately.

At step 240, the imaging data can be compared to each size in the set of sizes. Similarly to steps 232-236, size(s) then can be eliminated from the set of sizes for which the imaging data does not fall within the ranges of the respective size(s) at step 242. Finally, at step 244, a size can be selected from the set of sizes that has ranges closest to the imaging data.

Exemplary measurements of a user's body dimensions mapped to a set of sizes are illustrated in FIG. 10, FIG. 11, and FIG. 12, for example. A method can include determining simulated measurements of (1) the circumference around the bust and (2) the circumference around the rib cage just below the bust. The difference between the two values can be used to determine a cup size, and the second value can be used to determine a band size. For example, for each of the differences in the far left column of the chart in FIG. 10, cup sizes in U.S., European, and UK sizes are illustrated. The chart in FIG. 11 illustrates the range of band sizes for each cup size, for example. Further, the chart in FIG. 12 illustrates an exemplary relationship between cup size, band size, and the difference between the circumference around the bust and the circumference around the rib cage just below the bust.

For mastectomy patients, a method can include determining simulated measurements of (1) the circumference around the rib cage just below the bust and—instead of the circumference around the bust—(2) a distance from the breastbone through the fullest part of the breast to the center of the back. The second value then can be doubled, and the first value can be subtracted to determine a cup size.

Embodiments advantageously can include the use of a laptop or desktop computer with a built-in camera, another computing device, or another portable electronic device such as a smart phone or tablet, for example. An exemplary process and method can include a user's pressing "start" on a computer or other computing device, for instance. A voice or visual command then can instruct the user from the beginning to the end of the quick and easy process. Additionally, a voice command can explain the preparation required prior to using a "scanner" application according to an embodiment. A voice command then can also explain that the scanner application will only capture a view of the user's bust, side, and back (not her face or below her bust) and that the scan is required for the purpose of obtaining accurate measurements for her cup and band size. A voice command can instruct the user to remove her top, exposing her bare bust, if she believes her cup size is "D" or smaller. Further, a voice command can instruct the user who believes her cup size is "DD" or larger to wear a loose fitting and non-padded bra (one that is not tight and binding), allowing the user's breasts to be lifted while the scanner application gathers an accurate cup and band (back) measurement. In addition, a voice command can instruct a user has had a mastectomy or has breast asymmetry to wear their most comfortable fitting mastectomy bra with breast forms/prosthesis in place. In some circumstances, the larger breast measurement can be used in methods according to embodiments.

A voice command also can instruct the user to pin up her hair if the length is beyond her neck in order for the scanner application to acquire an unobstructed and accurate measurement of her back. A voice command then can instruct the user to stand in front of her computer or device, making sure that her bust is lined up within a diagram that is displayed on a screen or display, and position herself standing straight with her arms placed down to her sides. The user next can be instructed to begin rotating in place until instructed to stop by a voice command. Once the correct alignment is obtained by the scanner application, a voice command then can instruct the user to begin rotating slowly in place, completing a 360 degree turn. Once the scanner application gathers complete measurements, a voice command can instruct the user to stop, ending the quick and simple process.

A voice command next can confirm that the scanner application accepted the user's movements and that the measurements were accurately taken. The user also can be instructed to continue to the next step in the selection of the style of a bra before placing the completed item into a shopping cart, for example. The user also can have a choice to keep the user's measurements online in a personal shopping file for future use. A notice also can be provided to the user if the user loses or gains 10 pounds or more to complete another custom measurement. In some instances, a notice can be provided to a user to complete another custom measurement if the prior measurement was taken more than a certain number of days in the past, such as thirty days in the past.

Images captured from a laser scanning process or other scanning or imaging process can be processed for accurate measurement from the convenience of a computer or laptop, for example, using a combination (simultaneously) of: horizontal measurement, controlling the oscillating angle, vertical measurement, and 3-dimensional height imaging. Further, images can be deleted following their being analyzed and processed for measurement.

Embodiments can include operating software in sync with video-based technology for desired accuracy to offer custom fittings for women with all cup sizes and women with a mastectomy or deformity. An initial short and concise questionnaire can be used to help to collect data related to weight, height, and desired functionality and style of a bra. A method according to an embodiment can conclude with recommending suggested bra style(s) to achieve a desired effect and/or look to a customer and can offer a large variety of bras suitable to wear with a large variety of outer clothing.

An exemplary user interface 402 as displayed on a display 124 is illustrated in FIGS. 4-8, for example. Also displayed with the user interface 402 is a URL or other address input field 404. As illustrated in FIG. 4, for example, user interface 402 can include text and one or more images 406. The user interface 402 further can include one or more icons that cause the user interface 402 to update or change responsive to their selection, such as a BEGIN button 408 that allows a user to begin interacting with the user interface 402, a CONTINUE button 416 that indicates that the user desires to continue interacting with the user interface 402, and a CONTINUE TO RECOMMENDATIONS button 418 to show recommended brassieres to the user via the user interface 402, as illustrated in FIG. 4, FIGS. 5-7, and FIG. 8, respectively, for example. Further, as illustrated in FIG. 5, for example, a user interface 402 can include one or more text input fields 410, one or more drop-down menus 412, and one or more radio buttons 414.

For example, as illustrated in FIG. 4, the user interface 402 can inform a user that a proper fitting bra is an essential need for all women and that it is estimated that approximately 70-80 percent of all women wear an incorrectly fitted bra that is either too small or too big. The user interface 402 further can state that this can be due to lifestyle changes, such as: experiencing weight loss or weight gain, having a recent pregnancy, having begun exercising (body toning), experiencing menopause, or having had a mastectomy or any other surgery or other condition altering body dimensions or causing a deformity.

Figure 5B:
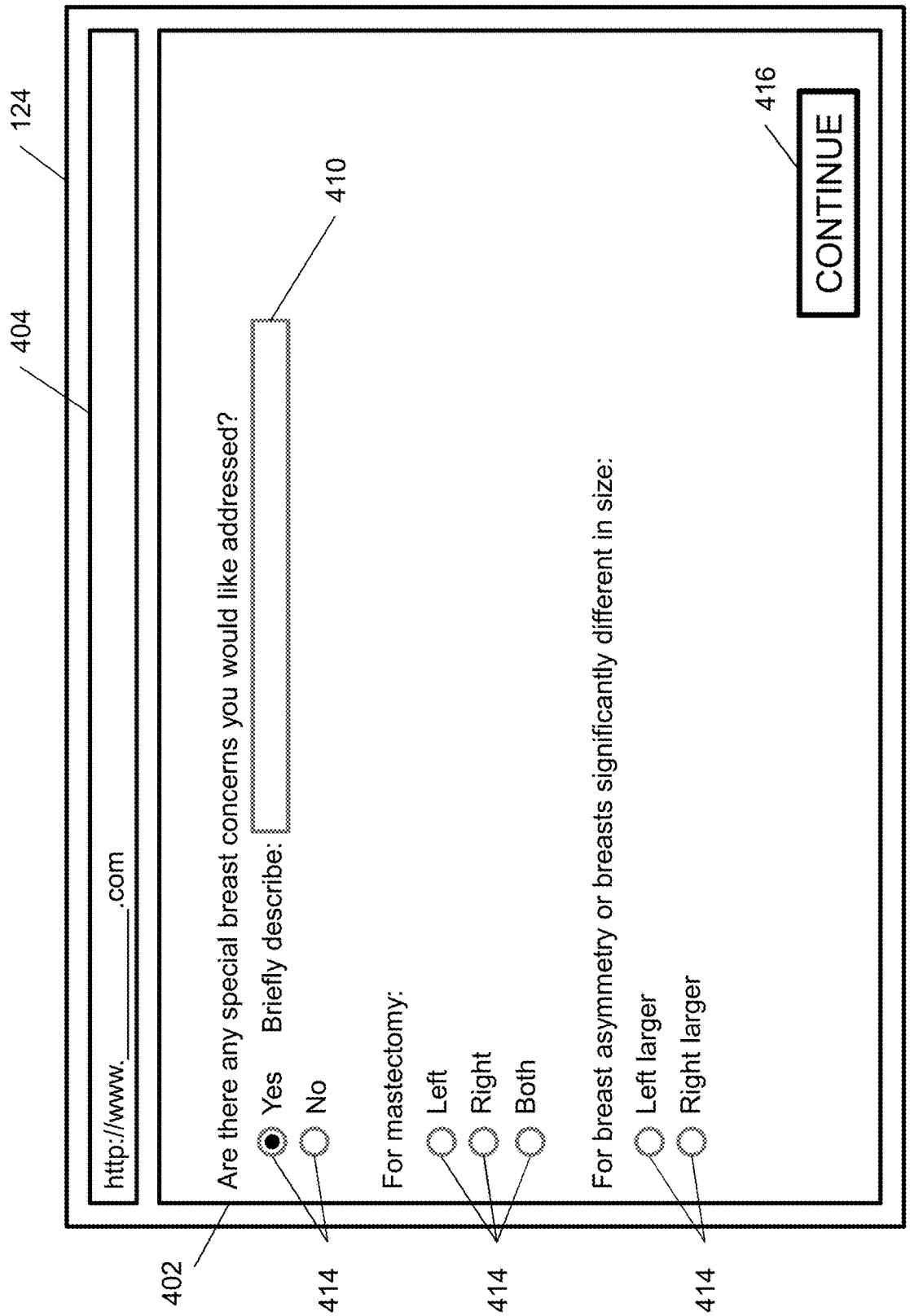

If the user selects the BEGIN button 408, the user interface 402 can update to generate a questionnaire. The questionnaire can ask, for example, for information including but not limited to the user's name, email address, age, currently worn brassiere size, whether the user is looking for a brassiere to wear with a particular outfit or garment and additional information regarding that outfit or garment, and any particular breast concerns, including mastectomy information (e.g., as illustrated in FIG. 5B) and prosthetics information to assist in pinpointing a desired effect (e.g., breast coverage, fit and functionality) with bra purchase. After the user inputs information using one or more text input fields 410, one or more drop-down menus 412, and one or more radio buttons 414, the user can choose to continue the process by selecting the CONTINUE button 216.

The user then can receive imaging instructions through the user interface 402, as illustrated in FIG. 6 and FIG. 7, for example. For instance, the user interface 402 can instruct the user to begin by removing only the user's top and bra and to stand facing the user's computing device 120, making sure that only the user's breasts appear on the screen or other display within a perforated or dotted outline that will be illustrated in the representation of the imaging device's view as images are acquired to indicate whether the user is positioned correctly relative to the imaging device 130.

The user interface 402 further can inform the user that once the user is positioned correctly as directed, a "voice command" will instruct the user to stand motionless while the first image is gathered for measurement. Further, the instructions can inform the user that a "voice command" will direct the user to begin rotating/turning slowly in place and that the user should continue turning slowly in place until a "voice command" directs the user to stop. The instructions additionally can instruct the user to repeat this process following "voice commands" as directed. Still further, the instructions can inform the user that once all required imaging is successfully captured, the user will hear a "voice command" announce that the imaging process is complete.

After images have been captured, the user interface 402 can display results to the user, as illustrated in FIG. 8, for example. The results can include displaying to the user the user's current bra size and the user's actual recommended bra size. Further, the user interface 402 can inform the user that it can display recommended brassiere(s) to the user upon the user's selection of a CONTINUE TO RECOMMENDATIONS button 418. If the user selects brassiere(s) of interest, as illustrated in FIG. 9, for example, the user can be given the option to purchase the selected brassiere(s).

Software according to an embodiment further can automatically request new measurements due to possible weight fluctuation or if the account has not been used for over four weeks.

Another remote electronic method to enhance measurement accuracy and speed of electronic brassiere fitting data according to an embodiment can include displaying a user interface 402 to a remote user computing device 120 associated with a user who wears a prosthetic device or has had a mastectomy. The remote user computing device 120 can be in communication with one or more imaging devices 130, such as a camera, a three-dimensional body scanner, an X-ray imaging device, a millimeter wave imaging device, or a magnetic resonance imaging device. Further, the user interface 402 can be formatted to receive input from the remote user computing device 120.

A method also can include receiving, using the one or more imaging devices 130, a set of physiological images of the user from the remote user computing device 120. The set of physiological images can include 360 degree images of the user's torso in some circumstances. A method then can include generating a recommended brassiere size responsive to receipt of brassiere fitting data from one or more data sources and the set of physiological images. The brassiere fitting data can include, for each available brassiere size, a set of ranges of: torso circumference measurements, bust circumference measurements, and shoulder to bust measurements. Further, generating the recommended brassiere size can include comparing the brassiere fitting data and the set of physiological images to the set of ranges for each available brassiere size, in some circumstances. A method further can include updating the user interface 402 to display the recommended brassiere size and one or more brassiere recommendations on the remote user computing device 120. The one or more brassiere recommendations can include purchasing information for one or more brassieres.

In some instances, the method further can include receiving a set of current user brassiere data from the remote user computing device 120, and generating the recommended brassiere size can be further responsive to the set of data. The set of current user brassiere data can include one or more of: the user's name, the user's email address, the user's home address, the user's age, outfit parameters, the user's current brassiere size, mastectomy information, and prosthetic information. Further, the outfit parameters can include one or more garment types, one or more garment styles, and one or more garment colors.

Embodiments also can include systems. A system 102 to remotely and electronically enhance measurement accuracy and speed of electronic brassiere fitting data according to an embodiment, for example, can include one or more processors 106 and non-transitory computer-readable medium 104, as illustrated in FIG. 1, for example. A system 102 further can include one or more input/output units 108. The non-transitory computer-readable medium 104 can be in communication with the one or more processors 106 and can have one or more computer programs stored therein that, when executed by the one or more processors, cause the system to take certain actions.

For example, the system 102 can display a user interface 402 to a remote user computing device 120 associated with a user who wears a prosthetic device or has had a mastectomy. The remote user computing device 120 can be located or positioned at a different location than a system 102. A system 102 then can be in communication with the remote user computing device 120 via a communication network 110, such as the Internet. The remote user computing device 120 also can include one or more processors 122, non-transitory computer-readable medium 128, and one or more input/output units 126. Further, the remote user computing device can include one or more displays 124. The remote user computing device 120 also can be in communication with one or more imaging devices 130.

Further, the user interface 402 can be formatted to receive input from the remote user computing device 120. A system 102 also can receive, using the one or more imaging devices 130, a set of physiological images of the user from the remote user computing device 120. A system 102 further can generate a recommended brassiere size responsive to receipt of brassiere fitting data from one or more data sources and the set of physiological images and update the user interface 402 to display the recommended brassiere size and one or more brassiere recommendations on the remote user computing device 120.

In some instances, the one or more imaging devices 130 can include one or more of: a camera, a three-dimensional body scanner, an X-ray imaging device, a millimeter wave imaging device, and a magnetic resonance imaging device. Further, the set of physiological images can include 360 degree images of the user's torso. The brassiere fitting data can include, for each available brassiere size, a set of ranges of: torso circumference measurements, bust circumference measurements, and shoulder to bust measurements. Additionally, generating the recommended brassiere size can include comparing the brassiere fitting data and the set of physiological images to the set of ranges for each available brassiere size.

In some circumstances, the one or more computer programs, when executed by the one or more processors 106, further cause a system 102 to receive a set of current user brassiere data from the remote user computing device 120. In addition, generating the recommended brassiere size can be further responsive to the set of data. The set of current user brassiere data can include one or more of: the user's name, the user's email address, the user's home address, the user's age, outfit parameters, the user's current brassiere size, mastectomy information, and prosthetic information. The outfit parameters can include one or more garment types, one or more garment styles, and one or more garment colors. Additionally, the one or more brassiere recommendations can include purchasing information for one or more brassieres.

Various embodiments can take into account different types of bras and their functionality, which can be considered in generating a recommended brassiere size and/or recommended brassiere. Brassiere styles can include: (i) a demi cup, sometimes referred to as a "half cup," that covers half to three quarters of the breast, creates cleavage and uplift, and is ideal for low-cut necklines, smaller cup sizes (A or B cup), and minimum support; (ii) push up, which offers extra lift while pushing breasts together, covers half of the breast, positions straps further apart, and provides maximum cleavage; (iii) plunge, in which the center of the bra is cut extremely low (in a V shape) and the sides of the cup are cut at an angle with padding at the bottom in order to push up the breasts and which does not increase the appearance of breast size; (iv) balconette, which is ideal for extremely low necklines, will not expose the entire breast (one quarter to one half), provides great lift, will not push breasts together, provides minimum cleavage enhancement, and features straps set far apart; (v) sport, which is wireless and seamless and minimizes breast movement by providing additional support while performing physical workouts and exercise; (vi) strapless, which provides minimum support, features no shoulder straps, and may require the wearer to go down a band size and up a cup size for a slightly better hold; (vii) maternity, which includes flaps that make nipples easily accessible for breastfeeding; (viii) mastectomy, which features a silicone-filled cup to create symmetry; (ix) bralette, which is ideal for smaller breasts, features built-in padding, provides minimum support, features a soft cup, and can be pullover; (x) full coverage, which features a full cup covering the entire breast, underwire, and extra coverage, is ideal for larger breasts, provides superb support, and assists in preventing back ache; (xi) t-shirt, which fits the breast smoothly, is lined with foam or lightly padded with polyfill, and conceals nipples under tight fitting clothing; (xii) side shaper, which provides shaping and support and features adjustable cushion straps that stay in place and 2-ply seamless cups creating a smooth look; (xiii) halter, which features straps that connect around the back of the neck, is cupless or partial cup, and can be worn with fairly low-cut clothing; (xiv) adhesive, also referred to as "stick-on," which is backless and strapless, adheres to the underside of the breast, and is often made of silicone or polyurethane; (xv) front closure, which includes any style of bra that fastens, closes, latches, zips, or clamps between breasts and is ideal for larger breasts; (xvi) convertible, which includes changeable straps for a variety styles (e.g., one shoulder, low back, strapless, halter, racer back); (xvii) peek-a-boo, a revealing style that exposes nipples and more of the breast than usual; and (xviii) minimizer, which reduces the appearance of average and larger breasts and provides full coverage.

In the various embodiments of the invention described herein, a person having ordinary skill in the art will recognize that various types of memory are readable by a computer, such as the memory described herein in reference to the various computers and servers, e.g., computer, computer server, web server, or other computers with embodiments of the present invention. Examples of computer-readable media can include but are not limited to: nonvolatile, hard-coded type media, such as read only memories (ROMs), CD-ROMs, and DVD-ROMs, or erasable, electrically programmable read only memories (EEPROMs); recordable type media, such as floppy disks, hard disk drives, CD-R/RWs, DVD-RAMs, DVD-R/RWs, DVD+R/RWs, flash drives, memory sticks, and other newer types of memories; and transmission type media such as digital and analog communication links. For example, such media can include operating instructions, as well as instructions related to the systems and the method steps described above and can operate on a computer. It will be understood by those skilled in the art that such media can be at other locations instead of, or in addition to, the locations described to store computer program products, e.g., including software thereon. It will be understood by those skilled in the art that the various software modules or electronic components described above can be implemented and maintained by electronic hardware, software, or a combination of the two, and that such embodiments are contemplated by embodiments of the present invention.

This application claims priority to and the benefit of U.S. Provisional Patent Application No. 62/312,715, titled "Scanner Application," filed Mar. 24, 2016, and U.S. Provisional Patent Application No. 62/369,493, titled "Systems and Methods to Remotely Fit Brassieres for Prosthetics Wearers and Mastectomy Patients," filed Aug. 1, 2016, each of which is hereby incorporated by reference.

In the drawings and specification, there have been disclosed embodiments of systems, interfaces, computer-readable media, and methods of the present invention, and although specific terms are employed, the terms are used in a descriptive sense only and not for purposes of limitation. The embodiments of systems, interfaces, computer-readable media, and methods of the present invention have been described in considerable detail with specific reference to these illustrated embodiments. It will be apparent, however, that various modifications and changes can be made within the spirit and scope of the embodiments of systems, interfaces, computer-readable media, and methods of the present invention as described in the foregoing specification, and such modifications and changes are to be considered equivalents and part of this disclosure.

The invention claimed is:

1. A remote electronic method to enhance measurement accuracy and speed of electronic brassiere fitting data for a mastectomy patient or a prosthetics wearer, the method comprising:

generating a user interface on a remote user computing device, wherein one or more imaging devices are built into the remote user computing device, including one or more of a three-dimensional body scanner, an X-ray imaging device, a millimeter wave imaging device, or a magnetic resonance imaging device;

transmitting imaging instructions to the remote user computing device via the Internet, the imaging instructions including one or more audio commands and commands configured to be displayed on the user interface associated with the remote user computing device;

receiving a set of current user brassiere data from the remote user computing device responsive to the transmitted imaging instructions;

providing a scanner application for obtaining a set of physiological images from the one or more imaging devices built into the remote user computing device;

receiving the set of physiological images from the scanner application that are associated with the mastectomy patient or the prosthetics wearer from the one or more imaging devices;

determining, based at least in part on the set of current user brassiere data and the set of physiological images, a physical user feature;

responsive to determining the physical user feature, selecting an adjusted measurement procedure, the adjusted measurement procedure configured to estimate one or more fitting parameters for a first physical user feature from the set of physiological images;

determining, using the adjusted measurement procedure, simulated measurements associated with the mastectomy patient or the prosthetics wearer, the simulated measurements estimating the one or more fitting parameters using, at least in part, available fitting parameters corresponding to second physical user features present in the set of physiological images and associated with the first physical user feature;

receiving brassiere fitting data from one or more data sources;

filtering the brassiere fitting data responsive to the set of current user brassiere data;

determining a first brassiere size responsive to filtering the brassiere fitting data;

responsive to determining the physical user feature, automatically modifying the first brassiere size based at least in part on the set of physiological images and the simulated measurements;

determining a recommended brassiere size responsive to modifying the first brassiere size; and providing, on a display screen with the user interface, an updated display including the recommended brassiere size along with one or more brassiere recommendations.

2. The method of claim 1, further comprising:

generating the one or more brassiere recommendations responsive to generating the recommended brassiere size; and transmitting the recommended brassiere size and the one or more brassiere recommendations to the remote user computing device via the Internet for display on the remote user computing device.

3. The method of claim 2, wherein the one or more brassiere recommendations include purchasing information for one or more brassieres.

4. The method of claim 1, wherein the set of current user brassiere data is received via the Internet, the set of data including one or more of: a user's name, the user's email address, the user's home address, the user's age, outfit parameters, the user's current brassiere size, mastectomy information, and prosthetic information.

5. The method of claim 4, wherein the outfit parameters include one or more garment types, one or more garment styles, and one or more garment colors.

6. The method of claim 1, wherein the set of physiological images include 360 degree images of a torso.

7. The method of claim 1, wherein the brassiere fitting data includes, for each available brassiere size, a set of ranges of at least one of: torso circumference measurements, bust circumference measurements, and shoulder to bust measurements.

8. The method of claim 1, wherein the set physiological of images include 360 degree images of a torso.

9. The method of claim 1, wherein the adjusted measurement procedure comprises:

determining a circumference around a rib cage just below a bust, the bust corresponding to the second physical user features;

determining a distance from a breastbone through a fullest part of the bust; and determining a cup size, based at least in part on the circumference and the distance.

10. The method of claim 9, wherein determining the cup size further comprises:

computing a first value, corresponding to two times the distance; and computing a second value, the second value being equal to the first value minus the circumference.

* * * * *

UNITED STATES PATENT AND TRADEMARK OFFICE
CERTIFICATE OF CORRECTION

PATENT NO. : 11,559,086 B1
APPLICATION NO. : 15/469209
DATED : January 24, 2023
INVENTOR(S) : Detra C. Aubert Page 1 of 1

It is certified that error appears in the above-identified patent and that said Letters Patent is hereby corrected as shown below:

In the Claims

Column 14, Line 37, please replace Claim 8 with the following:
-- 8. The method of Claim 7, wherein generating the recommended brassiere size further comprises:
 comparing the brassiere fitting data and the set of physiological images to the set of ranges for each available brassiere size. --

Signed and Sealed this
Twenty-eighth Day of November, 2023

Katherine Kelly Vidal
*Director of the United States Patent and Trademark Office*